(12) United States Patent
Tagawa et al.

(10) Patent No.: US 8,258,264 B2
(45) Date of Patent: Sep. 4, 2012

(54) PROCESS FOR PRODUCING ALBUMIN PREPARATION

(75) Inventors: Rikiichi Tagawa, Kumamoto (JP); Yoshihiro Hayase, Kumamoto (JP); Kota Maemura, Kumamoto (JP); Hisashi Tanigawa, Kumamoto (JP)

(73) Assignee: Juridical Foundation The Chemo-Sero-Therapeutic Research Institute, Kumamoto-ken (JP)

( * ) Notice: Subject to any disclaimer, the term of this patent is extended or adjusted under 35 U.S.C. 154(b) by 385 days.

(21) Appl. No.: 10/552,369

(22) PCT Filed: Apr. 8, 2004

(86) PCT No.: PCT/JP2004/005061
§ 371 (c)(1),
(2), (4) Date: Oct. 7, 2005

(87) PCT Pub. No.: WO2004/089402
PCT Pub. Date: Oct. 21, 2004

(65) Prior Publication Data
US 2006/0281903 A1    Dec. 14, 2006

(30) Foreign Application Priority Data

Apr. 9, 2003  (JP) ................................. 2003-105492
Apr. 9, 2003  (JP) ................................. 2003-105493

(51) Int. Cl.
  *C07K 1/00*   (2006.01)
  *C07K 14/00*  (2006.01)
  *C07K 16/00*  (2006.01)
  *C07K 17/00*  (2006.01)
(52) U.S. Cl. ...................................................... 530/369
(58) Field of Classification Search .................. None
  See application file for complete search history.

(56) References Cited

U.S. PATENT DOCUMENTS

| | | | |
|---|---|---|---|
| 4,540,573 A | 9/1985 | Neurath et al. | |
| 5,250,662 A * | 10/1993 | Chang | ........................... 530/364 |
| 5,277,818 A | 1/1994 | Matsuoka et al. | |
| 5,691,451 A | 11/1997 | Ohya et al. | |
| 5,779,905 A | 7/1998 | Morandi et al. | |
| 6,399,357 B1 * | 6/2002 | Winge | ........................... 435/239 |
| 2004/0110931 A1 * | 6/2004 | Holten | ........................ 530/388.1 |

FOREIGN PATENT DOCUMENTS

| | | |
|---|---|---|
| CA | 2277406 A1 | 10/2000 |
| EP | 0 428 758 A1 | 5/1991 |
| EP | 0976759 A2 | 2/2000 |
| JP | 01-305036 A | 12/1989 |
| JP | 04-234326 A | 8/1992 |
| JP | 06-279296 A | 10/1994 |
| JP | 07-126182 | 5/1995 |
| JP | H11-505233 | 5/1999 |
| JP | 2000-053581 A | 2/2000 |
| JP | 2002-114799 A | 4/2002 |
| JP | 2005-505313 | 2/2005 |
| JP | 02-191226 | 4/2008 |
| WO | 98/37086 A1 | 8/1998 |

OTHER PUBLICATIONS

Planova filters. http://www.asahi-kasei.co.jp/planova/en/product/filters.html, accessed online Jun. 4, 2008, 2 pages.*
Meltzer and Jornitz, eds., Filtration and Purification in the Biopharmaceutical Industry. Chapter 1, 1998, pp. 1-69 (Provided in 3 parts).*
Burnouf, T., "Chromatographic Removal of Viruses from Plasma Derivatives", *Developments in Biological Standardization*, 1993, vol. 81, pp. 199-209.
Search report in European Patent No. 04726619.2 by the European Patent Office on Mar. 10, 2011.

* cited by examiner

*Primary Examiner* — Marcela M Cordero Garcia
(74) *Attorney, Agent, or Firm* — Browdy and Neimark, PLLC

(57) ABSTRACT

An albumin preparation may be produced efficiently on a commercial basis that has reduced possibility of contamination of infectious viruses and has high safety and stability. The process according to the present invention comprises a step of filtration of a serum albumin-containing solution with a virus-removing membrane preferably with a pore size of 10 to 20 nm. In particular, said filtration is performed before heat treatment for inactivation of viruses. In a more preferable embodiment, said serum albumin-containing solution is treated with an anion exchanger and/or a prefilter before a step of said filtration.

6 Claims, 3 Drawing Sheets

PROCESS FOR PRODUCING ALBUMIN PREPARATION

TECHNICAL FIELD OF THE INVENTION

The present invention relates to the field of a medical drug. Specifically, the present invention relates to a process for preparing a serum albumin preparation, one of preparations of plasma fractions. More specifically, the present invention relates to a process for preparing a serum albumin preparation involving a step of filtration with a virus-removing membrane. The process for preparation of the present invention allows for efficient production of a serum albumin preparation with high safety and reduced possibility of contamination of infectious viruses.

BACKGROUND OF THE INVENTION

Serum albumin, a protein with a molecular weight of about $6.6 \times 10^4$ Da, consists of 585 amino acid residues and has an elliptic shape. It accounts for about 60% of the total proteins, is most abundant in plasma and is synthesized in the liver. It participates in maintenance of osmotic pressure of plasma collagen, counteraction of poison and maintenance of acid-base equilibrium. It also plays a role in transporting numerous drugs or chemical substances by binding thereto non-specifically.

Such albumin is formulated into an albumin preparation for use in therapy of burn, hypoalbuminemia due to lost of albumin caused by nephrotic syndrome and reduction of capacity for albumin synthesis, hemorrhagic shock, and the like. An albumin preparation, which includes Plasma Protein Fraction (PPF), is a protein preparation that contains as high a level of a protein as 4.4 to 25%, among which albumin accounts for 80% or more, or 96% or more. Its volume per preparation is also as large as 20 to 250 mL. Thus, a large quantity and volume of a protein needs be handled for production of an albumin preparation.

On the other hand, there is no denying a possibility that a protein, in particular a protein from the living body, more specifically a protein from blood, might be contaminated with various viruses such as AIDS virus, various hepatitis viruses, and human parvovirus B19. Accordingly, for production of a medicament using these proteins as a starting material, it is indispensable to incorporate a step of sufficiently removing or inactivating viruses.

For inactivation of viruses, a possibility of whose contamination in a preparation from blood, i.e. a blood preparation, is not denied, heat treatment has commonly been used. Alternatively, a solvent-detergent (SD) approach may also be used for inactivation of viruses in which special solvents and detergents are used (see Japanese Patent Publication No. 051116/1985). Viruses may also be removed by affinity chromatography, or ion exchange chromatography (see Developments in Biological Standardization, Vol., 81, 199-209 (1993)). However, all these approaches have both merits and demerits and each of individual approach alone would not likely provide complete inactivation or complete removal of viruses. Thus, it is accepted that plural approaches may effectively be used in combination.

An albumin preparation, a target of the present invention, has been subject to inactivation/removal of viruses by heating in a liquid state (at 60° C. for 10 hours) and alcoholic fractionation and its safety has been proved by its clinical use for over fifty years. However, in view of further promotion of safety, as a measure for inactivation/removal of pathogens such as viruses not being inactivated/removed even through the above processes or unknown pathogens such as viruses that have not yet been found, an approach for removal of these pathogens has been investigated using filtration with a virus-removing membrane. However, no such filtration with a virus-removing membrane has been practically introduced for production of an albumin preparation on a commercial basis.

DISCLOSURE OF THE INVENTION

Technical Problem to be Solved by the Invention

Filtration with a virus-removing membrane is intended to remove pathogens such as viruses that are larger than a pore size of the membrane from a medical preparation when the preparation is produced. However, a major problem met with removal of pathogens such as viruses from a proteinaceous solution using the membrane is that the membrane is clogged to let filtration be difficult or impossible.

A pore size of a virus-removing membrane may vary depending on a manufacturer or a standard of the membrane and is in a range of from 10 to 70 nm. On the other hand, a molecular weight of a protein to be passed through pores of a virus-removing membrane in filtration is 10 to about 1000 kDa, which is about the same size as that of a virus-removing membrane. The smaller a pore size of a virus-removing membrane is, the greater effects may be expected as smaller viruses may be captured and removed. However, depending on a size of a protein to be passed through pores of a virus-removing membrane, a protein and a virus will not be separated from each other. Accordingly, for filtration of a proteinaceous solution with a virus-removing membrane, a pore size of the membrane for use needs be selected while a size of a protein to be passed through the membrane is taken into consideration. Besides, even if a virus-removing membrane with an appropriate pore size is selected for use, a trace amount of an aggregate or a contaminating protein that may be present in a proteinaceous solution will not be able to pass through the pores of the membrane to fill up the pores, causing clogging of the membrane or disturbance of filtration. In particular, in case of filtration with a virus-removing membrane with a small pore size, i.e. 10 to 20 nm, a size of a protein that may pass through the membrane is quite small and hence the problem is to prevent clogging of the membrane from occurring, depending on a kind and an amount of a protein contained in filtrate.

In addition, for production of an albumin preparation, an amount of a protein to be treated is much higher than that of other plasma preparations. Therefore, for introduction of filtration with a virus-removing membrane, it should be considered in which step of a production process filtration may be performed or an aqueous albumin solution with what composition or property may be filtered. In addition, a quantity, a filtration area and a cost of a virus-removing membrane should also be considered for introduction of filtration. Thus, it is essential for industrial application to find out conditions where as small a quantity of an expensive virus-removing membrane as possible may be used for introduction of filtration process using a virus-removing membrane.

Means for Solving the Problems

An object of the present invention is to produce efficiently a preparation with high safety and reduced possibility of contamination of infectious viruses. In application of filtration with a virus-removing membrane, which has been used for removal of pathogens such as viruses in a chemical solution, to a production process of an albumin preparation in a commercial actual scale of production not attempted hitherto, the present inventors have found a good filtration property to complete the present invention.

Since a good filtration condition for filtration with a virus-removing membrane in production of an albumin preparation has not hitherto been provided, the present inventors have earnestly investigated so as to solve the problems as described above. As a result, the present inventors have found that a good filtration becomes possible by removing or reducing a contaminating protein with a size larger than a pore size of a virus-removing membrane, said protein causing clogging of the membrane, before filtration of an aqueous albumin-containing solution with the membrane.

In addition, the present inventors have found that a good filtration property could be obtained by performing filtration of an aqueous albumin-containing solution using a virus-removing membrane before a heat treatment in a liquid state at 60° C. for 10 hours or more in the presence of a heat-stabilizing agent for inactivation of viruses in a production process of albumin.

More Efficacious Effects than Prior Art

In filtration with a virus-removing membrane in accordance with the present invention, an albumin-containing solution before a heat treatment was found to exhibit a good filtration property. Besides, it was confirmed that pretreatment with an anion exchanger and/or prefiltration in a preferable embodiment may provide for an effect that a volume of filtration per area of a filter increases without manipulating chemical conditions of the solution. Thus, capacity of filtration of a large amount of an albumin solution with a small area of filter may allow for introduction of filtration with a virus-removing membrane to a production process of an albumin preparation in an industrial scale.

In accordance with a process for preparation of the present invention, in addition to removal/inactivation of viruses through the conventional alcoholic fractionation and heat treatment, a novel means of filtration with a virus-removing membrane becomes possible. An albumin preparation as obtained in accordance with the process of the present invention is more excellent in safety.

The present invention opens up a road to introduction of filtration with a virus-removing membrane to a production process of an albumin preparation since a good filtration condition for filtration with a virus-removing membrane has not hitherto been provided in production of an albumin preparation.

BEST MODE FOR CARRYING OUT THE INVENTION

Figure 1:
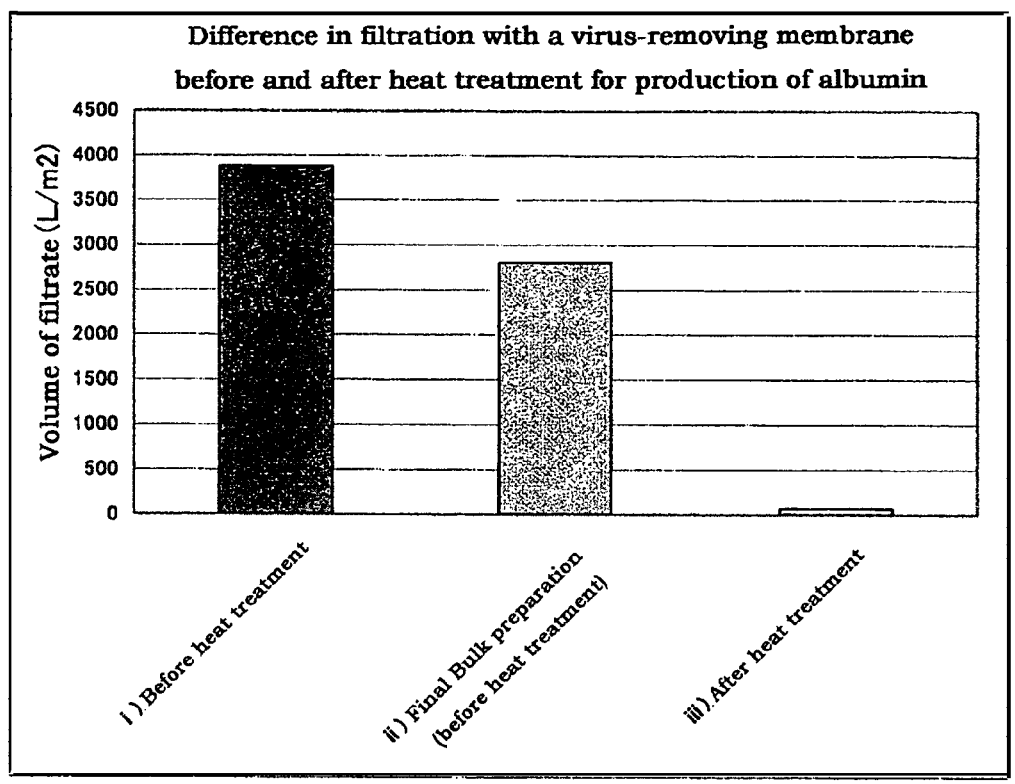
FIG. 1 shows filtration properties in filtration processes using a virus-removing membrane as incorporated into a process for preparing an albumin preparation in accordance with the present invention.

An albumin solution contains as a contaminating protein not only other proteins such as haptoglobin, transferrin and hemopexin but also an aggregate of albumin per se. In a heat treatment in a liquid state for production of an albumin preparation, although a heat-stabilizing agent is used, denaturation of a protein due to heating is inevitable and hence formation of a trace amount of an aggregate is observed in a liquid after a heat treatment. In addition, it is presumed that albumin per se may have changed its tertiary structure through interaction with a stabilizing agent such as sodium N-acetyltryptophan or sodium caprylate. These are thought to cause clogging of a membrane. There has hitherto not been reported, however, that albumin, due to a heat treatment, makes filtration with a virus-removing membrane difficult.

In a preferable embodiment, before performing filtration with a virus-removing membrane, an albumin solution may be pretreated by an anion exchanger treatment and/or prefiltration (removal size: 35 to 200 nm) so as to remove or reduce a contaminating protein to thereby allow for inhibition of clogging during filtration with a virus-removing membrane and for filtration of an albumin solution with a virus-removing membrane with a small pore size (10 to 20 nm) without a significant reduction in a flow rate, which consequently reduces a quantity of a virus-removing membrane and brings its suitable industrial application in production of an albumin preparation.

A source of albumin as an active ingredient of an albumin preparation in accordance with the present invention may be any including a mammal such as human, bovine or rabbit or culture cells using the genetic engineering technique. Among these, albumin from human may most practically be used including for instance a Fraction V from Cohn's method of ethanol fractionation.

A process for preparing an albumin preparation of the present invention may encompass any process that comprises a step of filtration of an aqueous albumin-containing solution as described above using a virus-removing membrane to remove possibly contaminating viruses. By performing a step of filtration of the present invention before a heat treatment for inactivation of viruses, however, a good filtration property may be obtained.

A virus-removing membrane as used herein may preferably have a pore size of 10 to 20 nm. Any virus-removing membrane may be used that meets with this criterion. A preferable virus-removing membrane may include those commercially available such as Planova 15N (Asahi Kasei Corporation), Ultipor VF-DV20 (Pall Corporation), Viresolve (Millipore Corporation), and the like.

Besides, the effect of the process of the present invention may be further enhanced by subjecting an aqueous albumin-containing solution to pretreatment by a charge-based isolation and removal with an anion exchanger and/or a size-based isolation and removal with a prefilter (removal size: 35 to 200 nm) so as to remove a contaminating protein that causes clogging, followed by filtration with a virus-removing membrane.

In a preferable embodiment of the present invention, pretreatment may be performed before a step of filtration with a virus-removing membrane, including pretreatment with an anion exchanger or pretreatment by prefiltration and a combination thereof. Although each pretreatment alone may provide a proper effect, enhanced effect is obtainable with a combination thereof. Specifically, each of the pretreatments may be done as described below.

(1) Pretreatment with an Anion Exchanger

An albumin-containing solution, in which pH, electric conductivity and a protein concentration are adjusted, is applied to an anion exchanger equilibrated with an appropriate buffer so that a contaminating protein contained in said solution may be removed through its adsorption to said anion exchanger. An anion exchanger for use may be an insoluble carrier bearing an anion exchange group including DEAE-Sepharose (Amersham Pharmacia), Q-Sepharose (Amersham Pharmacia), DEAE-TOYOPEARL (Tosoh Corporation), QAE-TOYOPEARL (Tosoh Corporation), and the like. A preferable anion exchanger is a strong anion exchanger such as Q-Sepharose and QAE-TOYOPEARL.

(2) Pretreatment by Prefiltration

An albumin-containing solution, in which pH and a protein concentration are adjusted, is passed through a prefilter (removal size: 35 to 200 nm) so that protein particles of a size larger than 35 to 200 nm that may cause clogging may be removed through capture by the prefilter. A prefilter for use includes a cartridge filter (Sartorius, Sartopore 2, 0.1 µm), a hollow fiber filter (Asahi Kasei Corporation, Microza, 0.1 µm), a porous membrane hollow fiber (Asahi Kasei Corporation, Planova, 35 nm), and the like. A preferable prefilter includes Sartopore 2 and Planova 35 nm.

In accordance with the present invention, an albumin preparation may be prepared, for instance, as described below.

(1) Preparation of Aqueous Albumin-Containing Solution

To a paste of Fraction V from Cohn's method of ethanol fractionation is added water for injection (The Japanese Pharmacopoeia) in an amount by weight of twice or more of the paste and the mixture is stirred to dissolve. The mixture is subject to ultrafiltration to remove alcohol and adjusted to pH 4 to 5 (preferably 4.4 to 4.6), EC 5 mS/cm or less (preferably 1.5 mS/cm or less), and a protein concentration of 5 to 15 w/v % (preferably 8 to 12 w/v %).

(2) Pretreatment with Ion Exchanger

The aqueous albumin-containing solution prepared in step (1) is applied to an anion exchanger [e.g. DEAE-Sepharose (Amersham Pharmacia), Q-Sepharose (Amersham Pharmacia), DEAE-TOYOPEARL (Tosoh Corporation), QAE-TOYOPEARL (Tosoh Corporation)] equilibrated with an acetate buffer with pH 4 to 5 (preferably 4.4 to 4.6) and EC 5 mS/cm or less (preferably 1.5 mS/cm or less) to recover eluate.

(3) Pretreatment with Filter

The aqueous albumin-containing solution pretreated in step (2) adjusted to a protein concentration of 5 to 15 w/v % (preferably 6 to 10 w/v %) and pH 6 to 7.5 (preferably 6.6 to 7.2) is filtered through a filter with a removal size of 35 to 200 nm to recover filtrate.

(4) Treatment in Accordance with the Present Invention: Passing Through Virus-Removing Membrane The aqueous albumin-containing solution adjusted to a protein concentration of 5 to 15 w/v % (preferably 6 to 10 w/v %) and pH 6 to 7.5 (preferably 6.6 to 7.2) is passed through Planova 15N (Asahi Kasei Corporation) to recover filtrate.

(5) Preparation of Bulk Solution

The solution recovered in step (4) is adjusted to a protein concentration of 5 to 30 w/v % (typically 5 or 20 to 25 w/v %). In case that a protein needs be concentrated, ultrafiltration was used. Sodium N-acetyltryptophan and sodium caprylate at 0.08 mmol/g protein are added to the solution. The solution is adjusted to pH 6.9±0.5 and filtered through a filter membrane with a pore size of 0.22 µm or less to prepare a final bulk solution.

(6) Heat Treatment and Filling

The final bulk solution is heated at 60.0±0.5° C. for 10 hours or more and each portions of a fixed amount are aseptically filled into a vial and sealed.

The present invention is explained in more detail by means of the following Preparation and Examples but should not be construed to be limited thereto.

Preparation (Preparation of Albumin Preparation)

(1) Preparation of Aqueous Albumin-Containing Solution

To a paste of Fraction V from Cohn's method of ethanol fractionation was added water for injection (The Japanese Pharmacopoeia) in an amount by weight of twice or more of the paste and the mixture was stirred to dissolve. The mixture was subject to ultrafiltration to remove alcohol and adjusted to pH 4.54, EC 1.5 mS/cm or less, and a protein concentration of 12 w/v %.

(2) Pretreatment with Ion Exchanger

The aqueous albumin-containing solution prepared in step (1) was applied to an anion exchanger [Q-Sepharose (Amersham Pharmacia)] equilibrated with an acetate buffer with pH 4.51 and EC 5 mS/cm or less to recover eluate.

(3) Pretreatment with Filter

The aqueous albumin-containing solution pretreated in step (2) adjusted to a protein concentration of 8 w/v % and pH 6.98 was filtered through a filter with a removal size of 100 nm to recover filtrate.

(4) Treatment in Accordance with the Present Invention: Passing Through Virus-Removing Membrane The aqueous albumin-containing solution adjusted to a protein concentration of 8 w/v % and pH 6.98 was passed through Planova 15N (Asahi Kasei Corporation) to recover filtrate.

(5) Preparation of Bulk Solution

The solution recovered in step (4) was adjusted to a protein concentration of 25 w/v %. In case that a protein needs be concentrated, ultrafiltration was used. Sodium N-acetyltryptophan and sodium caprylate at 0.08 mmol/g protein were added to the solution. The solution was adjusted to pH 6.9±0.5 and filtered through a filter membrane with a pore size of 0.22 µm or less to prepare a final bulk solution.

(6) Heat Treatment and Filling

The final bulk solution was heated at 60.0±0.5° C. for 10 hours or more and each portions of a fixed amount were aseptically filled into a vial and sealed.

EXAMPLE 1

Confirmation of Favorable Filtration Property of the Present Invention

In order to confirm effects of the present invention in production process of an albumin preparation, the aqueous albumin-containing solutions at each step were compared as described below. A filtration property was compared for the following three conditions: (i) the aqueous albumin-containing solution obtained after steps (1) through (3) before heat treatment was adjusted to a protein concentration of 8 w/v % and pH 4 to 9 and then subject to filtration with a virus-removing membrane at a constant pressure; and for comparison (ii) the aqueous albumin-containing solution obtained after steps (1) through (3) before heat treatment was concentrated so as to perform a step of preparation of a final bulk solution, adjusted again to a protein concentration of 8 w/v % and pH 7 and then subject to filtration with a virus-removing membrane at a constant pressure; and (iii) the aqueous albumin-containing solution obtained after steps (1) through (3) before heat treatment was concentrated so as to perform a step of preparation of a final bulk solution plus a step of heat treatment, adjusted again to a protein concentration of 8 w/v % and pH 7 and then subject to filtration with a virus-removing membrane at a constant pressure.

The results are shown in FIG. 1. As is clear from FIG. 1, it was found that the albumin solution before heat treatment in accordance with the present invention exhibited a superior filtration property to that of the albumin solution after heat treatment. Specifically, it was found that the albumin solution before heat treatment enabled filtration of about 50-folds more albumin than the albumin solution after heat treatment.

EXAMPLE 2

Confirmation of Effects of Pretreatment of the Present Invention

In order to confirm effects of pretreatment with an anion exchanger and/or prefiltration, the aqueous albumin-containing solutions obtained in step (1) of Preparation was subject to pretreatment in accordance with the present invention of either (1) treatment with an anion exchanger [Q-Sepharose (Amersham Pharmacia)] alone, (2) prefiltration [a cartridge filter (Sartorius, Sartopore 2, 0.1 μm)] alone, or (3) a combination of treatment with an anion exchanger [Q-Sepharose (Amersham Pharmacia)] and prefiltration [a cartridge filter (Sartorius, Sartopore 2, 0.1 μm)], or as a control (4) not subject to pretreatment. Each of the aqueous albumin-containing solutions was adjusted to a protein concentration of 8 w/v % with water for injection (The Japanese Pharmacopoeia), to pH 6.98 with 1 w/v % sodium hydroxide solution and was subject to filtration with a virus-removing membrane (Asahi Kasei Corporation, Planova 15N) at a constant pressure of 0.5 kgf/cm$^2$. The results are shown in FIG. 2 wherein a flux of each filtration is represented as a volume of the albumin solution per area of the membrane.

Figure 2:
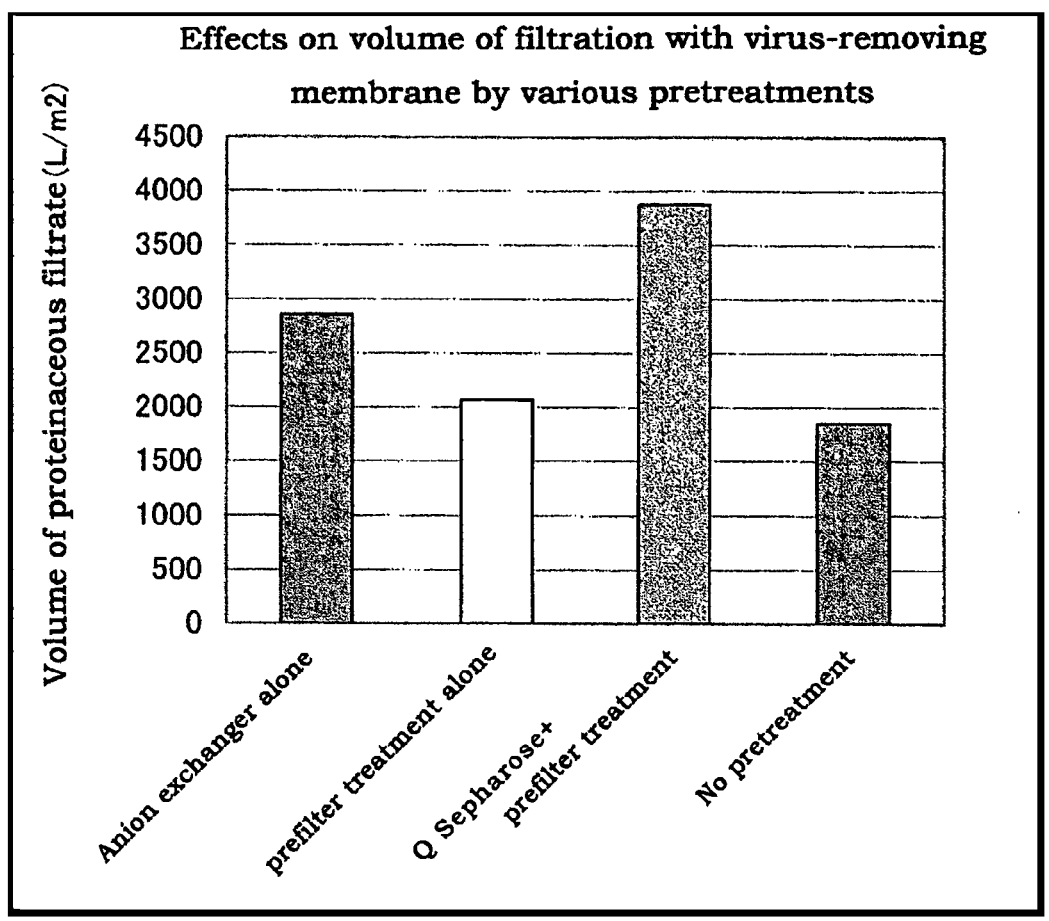
FIG. 2 shows filtration properties (effects on volume of filtration) with various pretreatments in filtration processes using a virus-removing membrane as incorporated into a process for preparing an albumin preparation in accordance with the present invention.

As is clear from FIG. 2, it was found that the albumin solution undergone pretreatment in accordance with the present invention exhibited a higher volume of filtration to that of the albumin solution with no pretreatment. Specifically, it was found that the albumin solution undergone pretreatment with a combination of an anion exchanger treatment and prefiltration enabled filtration of about twice more albumin than the albumin solution with no pretreatment.

EXAMPLE 3

Confirmation of Effects on Volume of Filtration by Various Types of Prefilter

In order to confirm effects on volume of filtration by various types of prefilter, the aqueous albumin-containing solutions obtained in step (2) of Preparation was subject to prefiltration in accordance with the present invention of either with (1) a cartridge filter (Sartorius, Sartopore 2, 0.1 μm), (2) a hollow fiber filter (Asahi Kasei Corporation, Microza, 0.1 μm), or (3) a porous membrane hollow fiber (Asahi Kasei Corporation, Planova, 35 nm), or as a control (4) not subject to pretreatment (prefiltration). Each of the aqueous albumin-containing solutions was adjusted to a protein concentration of 8 w/v % with water for injection (The Japanese Pharmacopoeia), to pH 6.98 with 1 w/v % sodium hydroxide solution and was subject to filtration with a virus-removing membrane (Asahi Kasei Corporation, Planova 15N) at a constant pressure of 0.5 kgf/cm$^2$. The results are shown in FIG. 3 wherein a flux of each filtration is represented as a weight of the albumin solution per area of the membrane.

Figure 3:
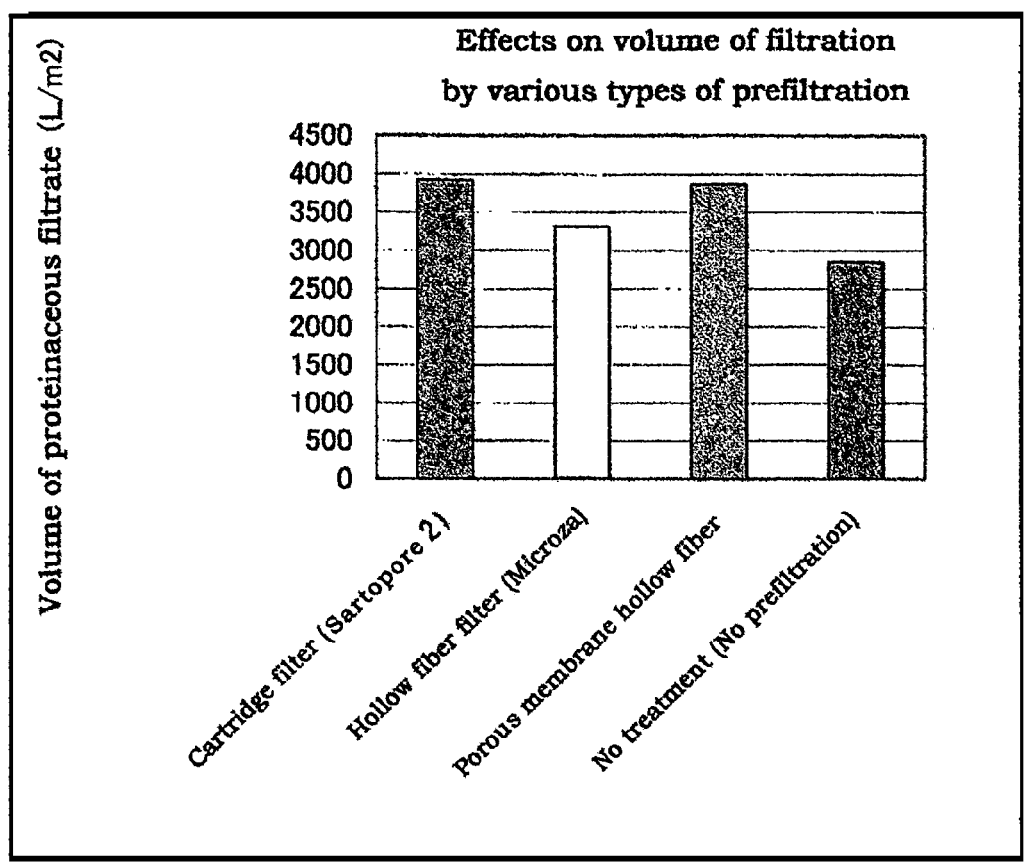
FIG. 3 shows effects on volume of filtration for various types of prefiltration in filtration processes using a virus-removing membrane as incorporated into a process for preparing an albumin preparation in accordance with the present invention.

As is clear from FIG. 3, it was found that a combination of the anion exchanger with any type of prefilters provided effects of an increased volume of filtration per area of the membrane. Specifically, it was found that a cartridge filter (Sartorius, Sartopore 2, 0.1 μm) and a porous membrane hollow fiber (Asahi Kasei Corporation, Planova, 35 nm) provided effects of a significantly increased volume of filtration per area of the membrane.

EXAMPLE 4

Confirmation of Effects on Removal of Viruses

In order to confirm effects of the present invention on removal of viruses, to 49 volumes of the aqueous albumin-containing solution obtained after steps (1) through (3) before subject to filtration with a virus-removing membrane was added either (i) 1 volume of pseudorabies virus (PRV), (ii) 1 volume of bovine virus diarrhea virus (BVDV), (iii) 1 volume of mouse encephalomyocarditis virus (EMCV), or (iv) 1 volume of porcine parvovirus (PPV). Each of these four virus-containing mixtures was filtered through a virus-removing membrane (Planova 15N, Asahi Kasei Corporation) and infection doses of virus are determined before and after filtration to confirm effects on removal of viruses. The results are shown in Table 1.

As is clear from Table 1, significant effects of filtration with a virus-removing membrane were revealed for every viruses tested.

TABLE 1

| Effects on removal of viruses by filtration with a virus-removing membrane | |
|---|---|
| | Effects on removal of viruses |
| i) PRV | ≧5.0 |
| ii) BVDV | ≧5.1 |
| iii) EMCV | ≧4.9 |
| iv) PPV | 4.1 |

Numeral: Infection doses of virus (logTCID$_{50}$/ml)

The invention claimed is:

1. The process for preparing an albumin preparation wherein an albumin-containing solution is subject to a step of filtration with a virus-removing membrane before a step of heat treatment sufficient to inactivate virus in a liquid state; wherein said process comprises treating the albumin-containing solution with an anion exchanger and a prefilter before a step of filtration with a virus-removing membrane.

2. The process for preparing an albumin preparation according to claim 1 wherein said virus-removing membrane used in a step of filtration with a virus-removing membrane has a pore size of 10 to 20 nm.

3. The process for preparing an albumin preparation of claim 1, wherein said prefilter has a pore size of 35 to 200 nm.

4. A process for pretreating an albumin-containing solution before a step of filtration with a virus-removing membrane which comprises treating said albumin-containing solution with an anion exchanger and a prefilter before a step of filtration of said albumin-containing solution with a virus-removing membrane.

5. The process for pretreating an albumin-containing solution of claim 4 wherein said prefilter used in said treatment has a pore size of 35 to 200 nm.

6. A process for preparing an albumin preparation substantially free of virus, comprising treating an initial albumin-containing solution with an anion exchanger and a prefilter, wherein the prefilter has a pore size 35 to 200 nm;

then subjecting the albumin-containing solution to filtration through a virus-removing membrane having a pore size of 10 to 20 nm; and next heat treating the albumin-containing solution to inactivate any remaining virus.

\* \* \* \* \*